United States Patent
Gelbein et al.

(10) Patent No.: US 7,368,617 B2
(45) Date of Patent: *May 6, 2008

(54) SELECTIVE HYDROGENATION OF ACETYLENES AND DIENES IN A HYDROCARBON STREAM

(75) Inventors: Abraham P. Gelbein, Falls Church, VA (US); Lawrence A. Smith, Jr., Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 611 days.

This patent is subject to a terminal disclaimer.

(21) Appl. No.: 10/983,433

(22) Filed: Nov. 8, 2004

(65) Prior Publication Data

US 2005/0090701 A1    Apr. 28, 2005

Related U.S. Application Data

(63) Continuation of application No. 10/385,677, filed on Mar. 12, 2003, now Pat. No. 6,867,338.

(60) Provisional application No. 60/364,886, filed on Mar. 15, 2002.

(51) Int. Cl.
   *C07C 5/03*    (2006.01)
(52) U.S. Cl. ...................... 585/259; 585/261
(58) Field of Classification Search ................ 585/259, 585/261
   See application file for complete search history.

(56) References Cited

U.S. PATENT DOCUMENTS

| | | | |
|---|---|---|---|
| 2,918,425 A | 12/1959 | Berger et al. | ................ 208/143 |
| 3,560,167 A | 2/1971 | Bruckner et al. | ............. 23/288 |
| 3,702,237 A | 11/1972 | Watkins | .................... 23/288 R |
| 4,126,539 A | 11/1978 | Derr, Jr. et al. | ............. 208/108 |
| 4,171,260 A | 10/1979 | Farcasiu et al. | ............ 208/240 |
| 4,194,964 A | 3/1980 | Chen et al. | ................. 208/108 |
| 4,283,271 A | 8/1981 | Garwood et al. | ............. 208/59 |

(Continued)

FOREIGN PATENT DOCUMENTS

WO    WO 97/40120 A1    10/1997

(Continued)

OTHER PUBLICATIONS

Trickle Hydrodesulfurization, The Oil and Gas Journal, Apr. 5, 1965, p. 116.

(Continued)

*Primary Examiner*—Thuan Dinh Dang
(74) *Attorney, Agent, or Firm*—Osha Liang LLP

(57) ABSTRACT

Acetylenes and dienes in a stream containing hydrogen, methane, $C_2$-$C_6$ olefins and paraffins, $C_2$-$C_6$ acetylenes and dienes, benzene, toluene, xylenes, and other $C_6$+ components are hydrogenated in a downflow boiling point reactor wherein the heat of reaction is absorbed by the liquid in the reactor which produces a vapor. Besides the feed to the reactor there is a recirculating stream which is fed at a rate sufficient to ensure that the catalyst particles within the reactor are wetted. A third stream, which is taken from a downstream distillation column, is fed to provide the make up mass corresponding to the mass evaporated in the reactor. The composition of the this third stream controls the steady state composition of the liquid flowing through the reactor.

3 Claims, 2 Drawing Sheets

U.S. PATENT DOCUMENTS

| | | | |
|---|---|---|---|
| 4,484,983 A | 11/1984 | Bannon | 203/42 |
| 4,990,242 A | 2/1991 | Louie et al. | 208/218 |
| 5,011,593 A | 4/1991 | Ware et al. | 208/213 |
| 5,190,730 A | 3/1993 | Smith, Jr. et al. | 422/109 |
| 5,409,599 A | 4/1995 | Harandi | 208/210 |
| 5,510,568 A | 4/1996 | Hearn | 585/834 |
| 5,554,275 A | 9/1996 | Harandi | 208/223 |
| 5,597,476 A | 1/1997 | Hearn et al. | 208/208 R |
| 5,714,640 A | 2/1998 | Bell et al. | 568/697 |
| 5,779,883 A | 7/1998 | Hearn et al. | 208/213 |
| 5,807,477 A | 9/1998 | Hearn et al. | 208/238 |
| 5,837,130 A | 11/1998 | Crossland | 208/213 |
| 5,863,419 A | 1/1999 | Huff, Jr. et al. | 208/237 |
| 5,925,685 A | 7/1999 | Adams et al. | 518/700 |
| 5,925,799 A | 7/1999 | Stanley et al. | 585/259 |
| 5,961,815 A | 10/1999 | Hickey et al. | 208/108 |
| 6,083,378 A | 7/2000 | Gildert et al. | 208/209 |
| 6,413,413 B1 | 7/2002 | Smith, Jr. | 208/213 |
| 6,416,658 B1 | 7/2002 | Maraschino et al. | 208/189 |
| 2002/0022754 A1 | 2/2002 | Boyer et al. | 585/265 |

FOREIGN PATENT DOCUMENTS

WO     WO 98/38265 A1     9/1998

OTHER PUBLICATIONS

M.L. Derrien, J.W. Andrews, P. Bonnifay, and J. Leonard, The IFP Selective Hydrogenation Process, Chemical Engineering Progress, vol. 70, No. 1, Jan. 1974, pp. 74-80.

Mordechay Herskowitz, Trickle-Bed Reactors; A Review, AlChE Journal, vol. 29, No. 1, Jan. 1983, pp. 1-18.

SELECTIVE HYDROGENATION OF ACETYLENES AND DIENES IN A HYDROCARBON STREAM

This is a continuation of application Ser. No. 10/385,677 filed on Mar 12, 2003 now U.S. Pat. No. 6,867,338 which claims the benefit of U. S. Provisional Application 60/364,886, filed Mar. 15, 2002.

BACKGROUND OF THE INVENTION

1. Field of the Invention

The present invention relates to a process for selectively hydrogenating acetylenes and dienes in a hydrocarbon stream. More particularly the invention relates to the selective hydrogenation of acetylenes and dienes in a hydrocarbon stream containing hydrogen, olefins and smaller amounts of acetylenes and dienes using a downflow boiling point reactor.

2. Related Information

The vapor product stream from the quench system of a hydrocarbon steam cracker typically consists mainly of hydrogen, methane, $C_2$-$C_6$ olefins and paraffins, $C_2$-$C_6$ acetylenes and dienes, benzene, toluene, xylenes, and other $C_6$+ components. Separation and recovery of the products according to carbon number is generally accomplished in a sequential distillation system after the first separation of hydrogen from the methane in a high pressure cold box system. The design of the distillation system is complicated by the fact that the differences in relative volatility of the olefins, acetylenes, and dienes of the same carbon number are small making it difficult to produce the pure olefin products. One method of circumventing this problem is to first separate the carbon number fractions and then to selectively hydrotreat each fraction to convert the acetylene and/or diene to its corresponding olefin or paraffin. This so called "back end" approach requires a separate hydrotreating system for each carbon number fraction as well as the addition of a requisite amount of hydrogen to each system. An alternative method is to hydrotreat the feed stream before separation using the contained hydrogen as the source of hydrogen for the conversion. This so-called "front end" approach has the advantage of removing a significant portion of the hydrogen from the feed stream to the cold box thereby reducing the size and refrigeration requirements of the cold box.

SUMMARY OF THE INVENTION

The present invention provides a "front end" hydrotreating system that allows for effective control of the temperature within a bed of catalyst which is hydrogenating acetylenes and dienes in a stream containing hydrogen, methane, $C_2$-$C_6$ olefins and paraffins, $C_2$-$C_6$ acetylenes and dienes, benzene, toluene, xylenes, and other $C_6$+ components. The invention utilizes a downflow boiling point reactor wherein the heat of reaction is absorbed by the liquid in the reactor which produces a vapor. Besides the feed to the reactor there is a recirculating stream which is fed at a rate sufficient to ensure that the catalyst particles within the reactor are wetted. A third stream, which is taken from a downstream distillation column, is fed to provide the make up mass corresponding to the mass evaporated in the reactor. The composition of the this third stream controls the steady state composition of the liquid flowing through the reactor. The composition of this stream may be controlled by selecting the point from the downstream distillation column from which the stream is drawn. The lower the draw point is in the column, the higher the boiling point of the components in the third stream. The steady state composition of the liquid flowing through the reactor along with the pressure determines the reactor temperature profile.

In a "boiling point reactor" a liquid phase is always maintained, even if the reaction components would be vaporized by the exothermic heat of reaction. In any reaction where the reaction stream is likely to be vaporized, an inert higher boiling component may be added to maintain a liquid phase.

DETAILED DESCRIPTION OF THE PREFERRED EMBODIMENT

Catalysts which are useful for the selective hydrogenation of acetylenes and dienes include palladium oxide supported on alumina. One such catalyst contains 0.34 wt. % palladium supported on ⅛ inch spheres designated G68C and supplied by Süd-Chemie (formerly United Catalyst Inc.). Another catalyst comprises 0.5 wt. % palladium supported on 8-12 mesh spheres and designated E144SDU as supplied by Calcicat, Catalyst and Performance Chemicals Division, Mallinckrodt, Inc. For best results the catalyst is supported in structured packing as disclosed in commonly owned U.S. Pat. No. 5,730,843. The catalyst may, however, be simply loaded into the reactor.

Figure 1:
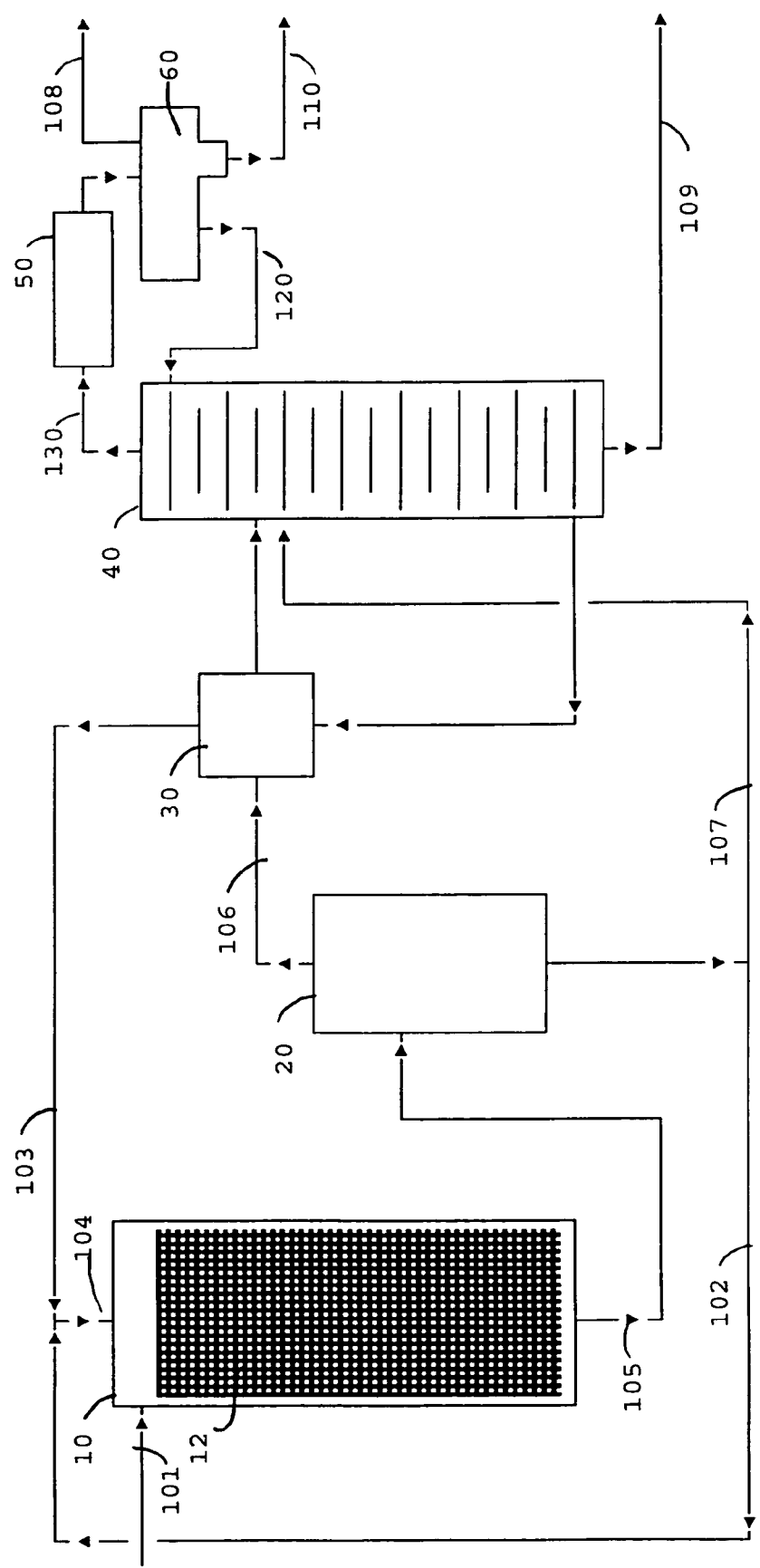
FIG. 1 is a flow diagram in schematic form of one embodiment of the invention.

Referring now to FIG. 1 selective hydrogenation of acetylenes and diolefins in a hydrocarbon stream containing significantly larger amounts (molar basis) of hydrogen and olefins than the acetylenes and diolefins is carried out in a downflow boiling point reactor. The downflow boiling point reactor, shown as column 10 is a vertically disposed reactor containing the particulate catalyst supported in a structured packing at 12. The gaseous feed stream is fed via flow line 101 to the top of the column 10. Also fed to the top of the reactor is liquid in flow line 104 which is a mixture of circulating stream in flow line 102 and stream in flow line 103 derived from. distillation column 40 as more particularly described below. Gas and liquid streams flow concurrently downward through the column with the flow regime being gas continuous. The concurrent flow of gas and liquid eliminates the possibility of a runaway reaction.

The reactor 10 is operated adiabatically so that the heat of reaction is accounted for by preferentially evaporating the lighter liquid phase components. Effluent from the reactor in flow line 105 is fed to vapor/liquid separator 20 where the vapor and liquid are separated. The heat content of the vapor in flow line 106 includes the heat of reaction generated in the reactor 10 while its mass rate is equal to the combined flows of the streams in flow lines 101 and 103 less slip stream 107 described below. Liquid in flow line 102 is fed back to the top of the reactor 10. The flow rate of the stream in flow line 102 is a variable and is maintained at least sufficient to ensure that the catalyst particles are fully wetted at all positions in the reactor 10. The stream in flow line 103 provides make up mass corresponding to the mass evaporated in the reactor that leaves the reactor system as part of the stream in flow line 106. The composition of the stream in flow line 103 controls the steady state composition of liquid flowing through the reactor 10. This is an important operating parameter that in combination with the reactor pressure determines the reactor temperature profile. A slip stream is taken by flow line 107 to control the liquid inventory in the vapor/liquid separator vessel 20.

Column 40 is a $C_5/C_6$ splitter. Feed to the column is the vapor from the separator 20 in flow line 106. It is heated by indirect heat exchange in exchanger 30 with the recirculating stream in flow line 103. The column 40 is designed to recover a vapor distillate fraction via flow line 108 which is essentially free of $C_6+$ components and a bottoms liquid product in flow line 109 which is essentially free of $C_5$ and lighter components. The overheads are taken via flow line 130 and passed through partial condenser 50 where the heavier components are condensed. The overheads are collected in receiver separator 60 where liquid hydrocarbon is withdrawn via flow line 120 and returned to the column 40 as reflux. Water is taken out via flow line 110. As noted distillate product is removed via flow line 108.

The draw off position or tray of the recirculating stream in flow line 103 is an operating variable. Moving the take off point further down the column increases the higher boiling components in the stream. Minimum operating pressure for the reactor 10 at a fixed temperature profile is achieved when the draw off is from the bottom stage of the column 40.

EXAMPLE

Figure 2:
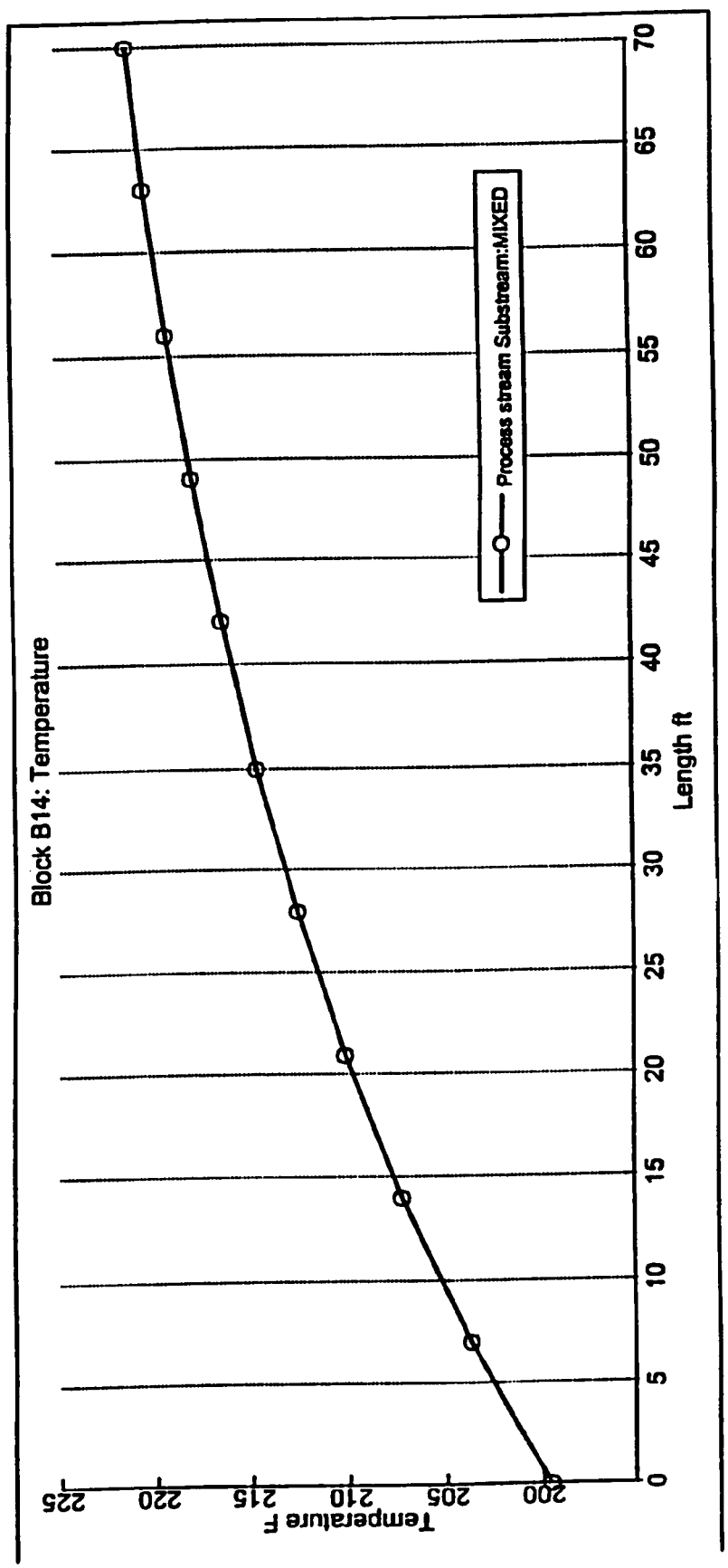
FIG. 2 is graphical representation of the temperature profile in a typical reactor of the present invention.

Feed to the system depicted in FIG. 1 is the vapor product from the quench tower of an olefins producing steam cracker after compression and acid gas ($CO_2$ and $H_2S$) removal. The reactor is loaded with approximately 14,000 $ft^3$ structured packing loaded with hydrogenation catalyst. Bed dimensions are approximately 15 ft diameter by 70 ft long. Operating conditions for the reactor are: reactor top/bottom pressure 250/240 psia; liquid recycle rate (stream in flow line 102) 4,000,000 lbs./hr.; slip stream in flow line 107 2243 lbs./hr. The distillation column 40 is a column configured with a 16.4 ft diameter 20 stage (theoretical) top section and 10.5 ft 20 stage (theoretical) bottom section. Design conditions for the distillation column 40 are: reflux ratio 0.18; reflux temperature 136° F., condenser pressure is 238 psia; column pressure drop is 2 psi; bottom stage side draw; decanter temperature 84° F. Heat and material balance results are given in TABLE I. Temperature profile across the reactor is given in FIG. 2.

TABLE 1

HEAT AND MATERIAL BALANCE

| | 101 | 102 | 103 | 104 | 105 | 106 | 107 | 108 | 109 | 110 |
|---|---|---|---|---|---|---|---|---|---|---|
| Temperature F. | 132 | 221.4 | 241.4 | 222.8 | 221.4 | 221.4 | 221.4 | 83.7 | 405.9 | 83.7 |
| Pressure psi | 250 | 250 | 250 | 250 | 240 | 240 | 240 | 238 | 240 | 238 |
| Vapor Frac | 1 | 0 | 0 | 0 | 0.379 | 1 | 0 | 27,809.5 | 0 | 0 |
| Mole Flow lbmol/hr | 29,994.6 | 52453.1 | 3,537.9 | 55,991.0 | 84,546.9 | 32,064.4 | 29.4 | 757,208 | 578.6 | 167.8 |
| Mass Flow lb/hr | 808,116.0 | 4,000,000 | 290,000 | 4,290,000 | 5,098,120 | 1,095,870 | 2,243 | 615,020 | 47,885 | 3,022 |
| Volume Flow cuft/hr | 718,016.6 | 94,069 | 6,677 | 100,746 | 995,976 | 901,853 | 53 | −115.6 | 1.323 | 49 |
| Enthalpy MMBtu/hr | −37.8 | −34.5 | −1.4 | −35.9 | −73.7 | −39.2 | 0.0 | | 6.0 | −20.6 |
| Mass Flow lb/hr | | | | | | | | 6,360 | | |
| H2 | 9,260.1 | 119 | 0 | 119 | 6,479 | 6,360 | 0 | 1,541 | 0 | 0 |
| Co | 1,540.9 | 58 | 0 | 58 | 1,599 | 1,541 | 0 | 0 | 0 | 0 |
| Methane | 118,468.5 | 9286 | 0 | 9,286 | 127,755 | 118,463 | 5 | 118,468 | 0 | 0 |
| Acetylen | 4,280.8 | 203 | 0 | 203 | 978 | 775 | 0 | 775 | 0 | 00 |
| Ethylene | 242,593.7 | 49,952 | 0 | 49,952 | 293,900 | 243,920 | 28 | 243,948 | 0 | 0 |
| Ethane | 52,743.4 | 14,705 | 0 | 14,705 | 70,045 | 55,332 | 8 | 55,340 | 0 | 0 |
| Meacetyl | 5,139.0 | 666 | 0 | 666 | 1,410 | 744 | 0 | 744 | 0 | 0 |
| Propadie | 5,197.5 | 2,583 | 0 | 2,583 | 5,743 | 3,158 | 1 | 3,160 | 0 | 0 |
| Propylen | 141,595.4 | 87,281 | 0 | 87,281 | 233,196 | 145,866 | 49 | 145,915 | 0 | 0 |
| Propane | 4006.4 | 3,996 | 0 | 3,996 | 10,556 | 6,558 | 2 | 6,560 | 0 | 0 |
| Butadien | 40,018.2 | 6,172 | 0 | 6,172 | 10,557 | 4,382 | 3 | 4,385 | 0 | 0 |
| T-Butene | 15317.0 | 23,503 | 0 | 23,503 | 38,820 | 15,304 | 13 | 15,317 | 0 | 0 |
| 1-Butene | 15672.9 | 69,511 | 0 | 69,511 | 121,641 | 52,091 | 39 | 52,130 | 0 | 0 |
| Cis2Bute | 15148.4 | 25,180 | 1 | 25,181 | 40,330 | 15,136 | 14 | 15,149 | 0 | 0 |
| Isobuten | 15705.2 | 20,525 | 0 | 20,525 | 36,230 | 15694 | 12 | 15,705 | 0 | 0 |
| Isobutan | 6571.8 | 7,591 | 0 | 7,591 | 14,163 | 6,568 | 4 | 6,572 | 0 | 0 |
| Butane | 6,368.8 | 10,212 | 0 | 10,212 | 17,104 | 6,886 | 6 | 6,892 | 0 | 0 |
| 1Pentene | 37318.5 | 140,912 | 2,356 | 143,268 | 190,449 | 49,457 | 79 | 46,978 | 203 | 0 |
| Hexane | 10179.2 | 471,367 | 64,831 | 536,198 | 546,377 | 74,746 | 264 | 1,669 | 8,509 | 0 |
| Octane | 1895.8 | 230,387 | 6,998 | 237,386 | 239,281 | 8,764 | 129 | 0 | 1,895 | 0 |
| Benzene | 27,486.7 | 1,826,330 | 167,100 | 1,993,430 | 2,020,920 | 193,560 | 1,024 | 227 | 27,258 | 0 |
| Toluene | 7,304.7 | 782,027 | 29,107 | 811,133 | 818,437 | 35,971 | 439 | 0 | 7,303 | 0 |
| M-xylene | 54.9 | 9,352 | 157 | 9,509 | 9,565 | 207 | 5 | 0 | 55 | 0 |
| O-oxylene | 41.5 | 7,618 | 112 | 7,729 | 7,771 | 149 | 4 | 0 | 42 | 0 |
| P-xylene | 58.9 | 9,860 | 170 | 10,029 | 10,089 | 223 | 6 | 0 | 59 | 0 |
| Ethylbz | 72.5 | 11,603 | 215 | 11,818 | 11,892 | 282 | 7 | 0 | 73 | 0 |
| Styrene | 34.0 | 6,293 | 90 | 6,383 | 6,417 | 121 | 4 | 0 | 34 | 0 |
| Water | 4,266.7 | 11,299 | 7 | 11,306 | 15,573 | 4,268 | 6 | 1,244 | 1 | 3,022 |
| PD | 8,127.7 | 715 | 26 | 742 | 966 | 250 | 0 | 222 | 3 | 0 |
| Isoprene | 7,499.2 | 622 | 29 | 651 | 808 | 185 | 0 | 154 | 3 | 0 |
| Hexadien | 4,147.5 | 85,000 | 11,044 | 96,044 | 98,172 | 13,124 | 48 | 657 | 1,472 | 0 |
| Hexene | 0.0 | 56,107 | 7,337 | 63,444 | 65,512 | 9,374 | 31 | 1,130 | 939 | 0 |
| Pentane | 0.0 | 18,965 | 419 | 19,384 | 25,388 | 6,412 | 11 | 5,967 | 37 | 0 |

The invention claimed is:

1. A process for the hydrogenation of acetylenes and dienes in a stream containing hydrogen, methane, $C_2$-$C_6$ olefins and paraffins, $C_2$-$C_6$ acetylenes and dienes, benzene, toluene, xylenes, and other $C_{6+}$ components comprising passing said stream over a hydrogenation catalyst contained in a downflow boiling point reactor having a top and a bottom wherein the downflow boiling point reactor is operated at the boiling point of the mixture and the heat of reaction is absorbed by the boiling liquid and where a portion of the acetylenes and dienes are converted to their corresponding olefins and paraffins of the same carbon number, recovering an effluent containing liquid and vapor from the bottom of the boiling point reactor, feeding the vapor in said effluent to a $C_5/C_6$ splitter where $C_5$ and lighter material are taken as overheads and $C_6$ and heavier material is taken as bottoms and a side draw is taken from said $C_5/C_6$ splitter and fed to the top of the downflow boiling point reactor.

2. The process according to claim 1 wherein a steady state composition of the liquid flowing in said downflow boiling point reactor is controlled by the location of the draw point of said side draw along the height of said $C_5/C_6$ splitter.

3. The process according to claim 2 wherein said side draw is taken from the bottom stage of said $C_5/C_6$ splitter.

* * * * *

UNITED STATES PATENT AND TRADEMARK OFFICE
CERTIFICATE OF CORRECTION

| | |
|---|---|
| PATENT NO. | : 7,368,617 B2 |
| APPLICATION NO. | : 10/983433 |
| DATED | : May 6, 2008 |
| INVENTOR(S) | : Lawrence A. Smith, Jr. et al. |

Page 1 of 1

It is certified that error appears in the above-identified patent and that said Letters Patent is hereby corrected as shown below:

In the Claims:

In Claim 1, column 5, line 12, "olefms" should be --olef<u>ins</u>--.

Signed and Sealed this

Twenty-second Day of July, 2008

JON W. DUDAS
*Director of the United States Patent and Trademark Office*